# (12) United States Patent
Kwon et al.

(10) Patent No.: US 7,250,432 B2
(45) Date of Patent: Jul. 31, 2007

(54) PHARMACEUTICAL COMPOSITIONS OF DIARYL-ISOXAZOLE DERIVATIVES FOR THE PREVENTION AND TREATMENT OF CANCERS

(75) Inventors: Byoung-Mog Kwon, Daejeon (KR); Kwang-Hee Son, Daejeon (KR); Dong-Cho Han, Daejeon (KR); Sang-Ku Lee, Daejeon (KR); Ki-Deok Shin, Daejeon (KR); Sun-Bok Jeon, Chungju (KR); Jung-Hoon Oh, Yeonki-kun (KR)

(73) Assignee: Korea Research Institute of Bioscience and Biotechnology, Daejeon-Si (KR)

( * ) Notice: Subject to any disclaimer, the term of this patent is extended or adjusted under 35 U.S.C. 154(b) by 100 days.

(21) Appl. No.: 10/969,291

(22) Filed: Oct. 20, 2004

(65) Prior Publication Data

US 2005/0131036 A1    Jun. 16, 2005

(30) Foreign Application Priority Data

Dec. 11, 2003  (KR) .................... 10-2003-0090411

(51) Int. Cl.
*A61K 31/42* (2006.01)
*C07D 261/06* (2006.01)
(52) U.S. Cl. .................... 514/378; 548/240; 548/247
(58) Field of Classification Search ............. 548/240, 548/247; 514/378
See application file for complete search history.

(56) References Cited

OTHER PUBLICATIONS

Khilya et al (1990): STN International HCAPLUS database, Columbus (OH), accession No. 1990:631246.*
P. Friedl et al., "Tumour-Cell Invasion And Migration: Diversity And Escape Mechanisms," May 2003, Nature, 3:362-374.
J.L. Arbiser et al., "Oncogenic H-ras stimulates tumor angiogenesis by two distinct pathways," Feb. 1997, Proc. Natl. Acad., Sci. USA, 94:861-866.
J. Folkman et al., "Angiogenic Factors," Jan. 1987, Science, 235:442-447.
L.A. Liotta et al., "Cancer Metastasis and Angiogenesis: An Imbalance of Positive and Negative Regulation," Jan. 1991, Cell, 64:327-336.
M.S. O'Reilly et al., "Angiostatin: A Novel Angiogenesis Inhibitor That Mediates the Suppression of Metastases by a Lewis Lung Carcinoma," Oct. 1994, Cell, 79:315-328.
T. Fotsis et al., "Genistein, a dietary-derived inhibitor of in vitro angiogenesis," Apr. 1993, Proc. Natl. Acad. Sci. USA, 90:2690-2694.
F.M. Uckun et al., "Biotherapy of B-Cell Precursor Leukemia by Targeting Genistein to CD19-Associated Tyrosine Kinases," Feb. 1995, Science, 267:886-891.

* cited by examiner

*Primary Examiner*—Golam M. M. Shameem
(74) *Attorney, Agent, or Firm*—Gates & Cooper LLP

(57) ABSTRACT

The present invention relates to a pharmaceutical composition for the prevention and the treatment of cancers containing diaryl-isoxazole derivatives as an effective ingredient. Diaryl-isoxazole derivatives of the present invention inhibit metastasis of breast cancer cell lines and angiogenesis, so that they can be produced as a metastasis inhibitor and further as a pharmaceutical composition for the prevention and the treatment of angiogenesis related diseases including cancers, rheumatoid arthritis, psoriasis, or angiogenesis diseases caused in eyeball, etc.

3 Claims, 4 Drawing Sheets

[Figure 1]
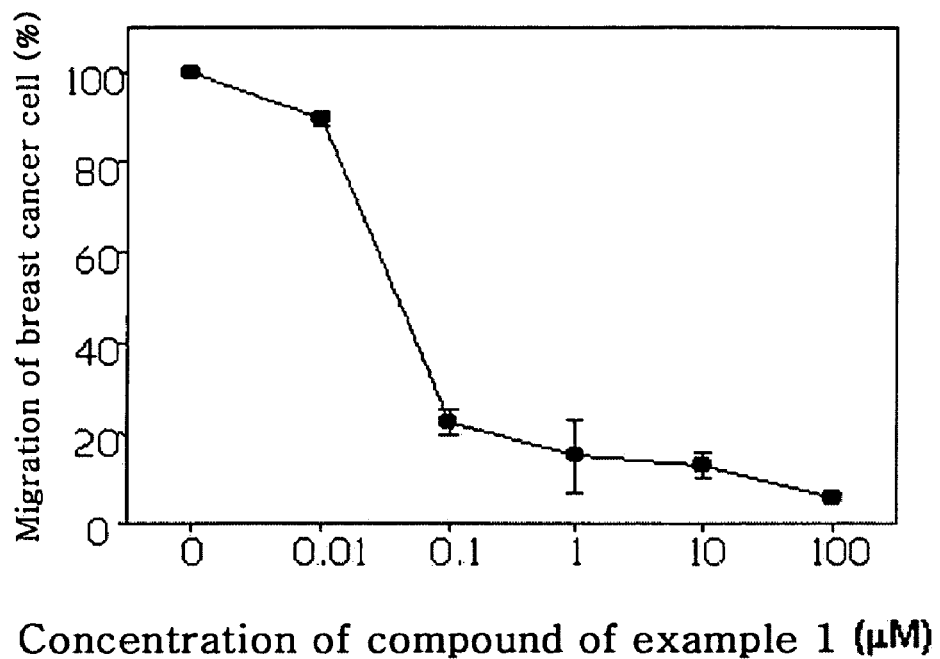
Concentration of compound of example 1 (μM)

[Figure 2]
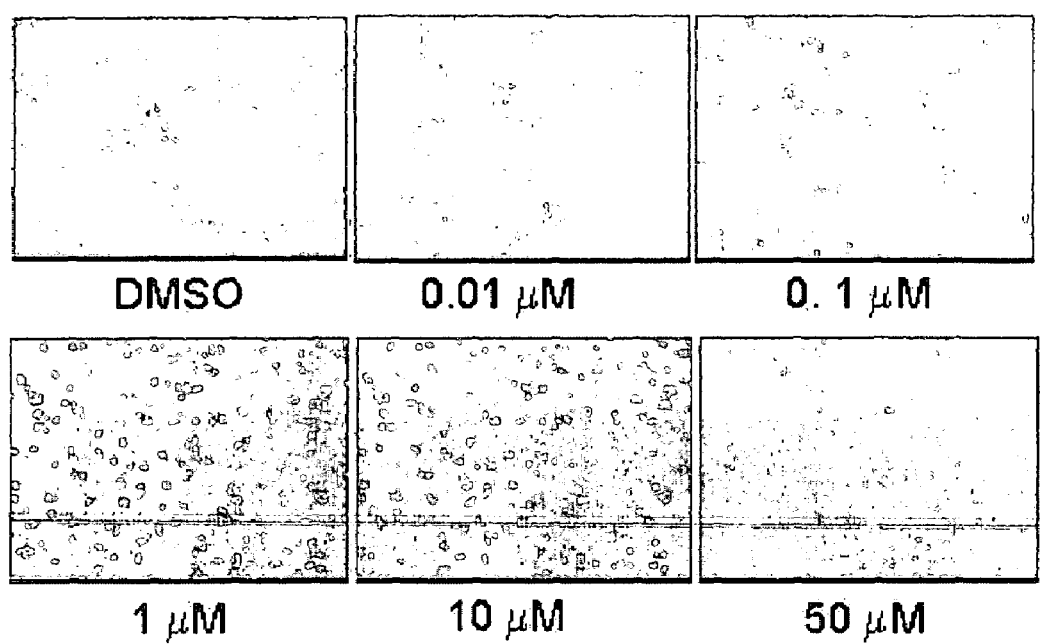

[Figure 3]
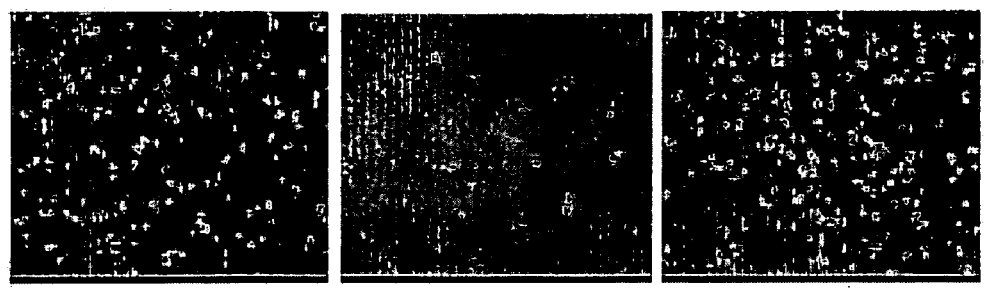
Example 1　　　　Example 2　　　　Example 3
Example 4　　　　Example 5　　　　Example 6

[Figure 4]
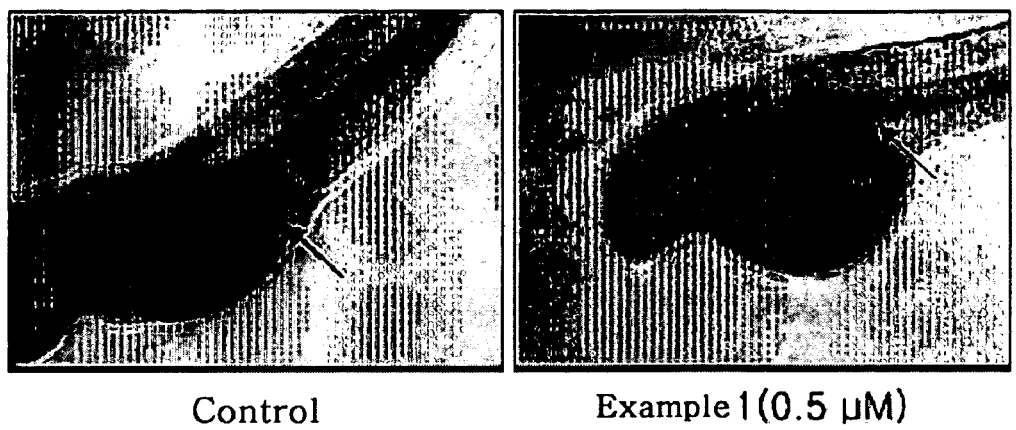
Control　　　　　Example 1 (0.5 μM)

PHARMACEUTICAL COMPOSITIONS OF DIARYL-ISOXAZOLE DERIVATIVES FOR THE PREVENTION AND TREATMENT OF CANCERS

This application claims benefit of priority to Korean Patent Application Number 10-2003-0090411, filed Dec. 11, 2003, the entire contents of which are incorporated herein by reference. Throughout this application, various references are cited. The contents of these references are incorporated herein by reference to more fully describe the state of the art pertaining to the invention disclosed herein.

FIELD OF THE INVENTION

The present invention relates to a pharmaceutical composition for the prevention and the treatment of cancers containing diaryl-isoxazole derivatives as an effective ingredient.

BACKGROUND

Cancer is caused by uncontrolled abnormal cell growth, and cancer cells infiltrate into normal tissues or organs around to destroy them and take over the places for its proliferation, even resulting in taking the life of an individual.

Although a remarkable progress has been made in studies of an oncogene and a tumor suppressor gene as well as regulations of cell cycle or apoptosis, cancer development is still on the increase as civilization advances. The treatment of cancer, for now, depends on surgical operation, radiotherapy and chemotherapy including administration of over 40 kinds of anticancer agents having strong cytotoxicity. However, those treatment methods are limited in use, meaning they are applicable to only cancer patients in early stage or with some specific cancers. So, cancer induced death is also on the increase.

The biggest threat of cancer to a life is metastasis, leading an individual to death. Surgical operation has been widely performed to treat cancer but it is not much help to treat transferred cancer cells, even after primary cancer has been removed. Therefore, conquering a cancer means a fight with metastasis.

Cell migration is involved in many stages of metastasis complicatedly; first, it is involved in early stage when cancer cells are transferred from the birth place into a blood vessel by way of extracellular matrix (ECM), second, it plays a role in transfer of cancer cells from the second metastatic tissues to outside blood vessels, and next, it is involved in the movement of vascular endothelial cells in neo-vasculatures.

The polarity of a transferring cell is induced by a signal receptor activated by a cell migrating inducer. The front end of a cell is attached to extracellular matrix by integrin with extension of cell membrane by polymerization of actin. At this time, strong contraction is caused between actin polymers by the bond of myosin with an actin polymer, giving a cell strong contraction. The direction of cell migration is determined by the difference between front end and back end of a cell in adhesive power. When adhesion of front is bigger than that of rear, the rear part of a cell is apart from extracellular matrix, making the cell move forward. On the contrary, when adhesion of front is weaker than that of rear, a cell stays at the place. Protrusions (Lamellipoda, Filapoda) having different structural morphology were formed by a signal transmission molecule activated by cell migrating signal receptor. Such different protrusions include actin in the form of a string and a set of protein having different structures and signals, and further lead reciprocal relation with ECM [Peter Friedl, et al., Nature Cancer Review, 2003, 3: 362].

The goal of an anticancer agent tracing the movement of cancer cell is also inhibiting metastasis. Inhibition of cell migration is not the final goal, but must be a realistic approach to extend life of a cancer patient. A tumor in primary stage can be simply and completely removed by surgical operation, regardless of the region, but once it transfers into other regions, surgical operation is not much help. If diagnosis is made after primary stage, cancer cells will be spread through blood vessels already and furthermore, a tiny colony might be generated at the second or at the third region. In that case, successful treatment of cancer cannot be expected by surgical operation only. Actually, there are lots of cases giving up surgical treatment because of metastasis. In those cases, an anticancer agent is administered, under the condition of inhibiting the movement of cancer cells, to induce apoptosis of cancer cells to extend life span of a patient. Thus, the development of a cancer cell movement inhibitor leads to the development of a novel anticancer agent and can be important assets for the study of cell movement.

Angiogenesis means whole process forming a new blood vessel from an existing blood vessel, and is accompanied indispensably by metastasis to a malignant tumor [Jack L. Arbiser, et al., Proc. Natl. Aced. Sci. USA, 1997, 94: 861]. Angiogenesis inhibitor has drawn our attention as one of attractive approaches to develop a novel anticancer agent. And the reasons of the importance or the attraction of angiogenesis inhibitor are as follows; first, angiogenesis is indispensable for primary tumor or metastatic tumor which means cancer cells are supplied with nutrition and oxygen through newly formed blood vessels and not growing larger than 1~2 $mm^3$ without the supply. During angiogenesis, primary tumor cells infiltrate into blood vessels and move to other regions, resulting in metastatic tumor. So, an angiogenesis inhibitor can be applied to any solid tumor. Second, the conventional chemotherapy is a way to treat cancer by taking advantage of fast growing speed of cancer cells, so that it shows cytotoxicity not only to cancer cells but also to bone marrow cells or gastrointestinal cells having comparatively fast turn over. But, an angiogenesis inhibitor carries less side effects even after long-term administration. In addition, another problem of the conventional chemotherapy is resistance since it is targeting transformed cancer cells. But, an angiogenesis inhibitor aims at treating a normal blood vessel, creating less chance of resistance. Third, one blood vessel is able to deliver nutrition and oxygen to hundreds of cancer cells, so even one-time inhibition of angiogenesis affects a great number of cancer cells. The advantage of drug delivery is the last reason. Precisely, under the conventional chemotherapy, an anticancer agent is to flow out of a blood vessel to kill cancer cells. On the contrary, an angiogenesis inhibitor can directly contact vascular endothelial cells, making drug delivery easy.

Dr. Folkman at Harvard Medical School hypothesized in early 1970s that a cancer cell secrets a specific factor to induce angiogenesis. After that, it was proved by many research groups including Dr. Folkman's team that angiogenesis plays an important role in metastasis, and further an angiogenesis-inhibiting factor was identified [J. Folkman, et al., *Science,* 1987, 235: 442]. In 1985, angiogenin, an angiogenesis inducer, was first found in secreting fluid of human adenocarcmoma cells by Dr. Vallee, et al., at Harvard medical school. A solid tumor is supplied with nutrition and excretes wastes through newly formed blood vessels around to be growing and cancer cells transfer to other regions such as lung, liver, etc., through circulatory system [L. A. Liotta, et al., *Cell,* 1991, 64: 327]. It was also reported that angiostatin, an angiogenesis inhibitor, suppresses growth and transfer of lung cancer cells [M. S. O'Relly, et al., *Cell,* 1994, 79: 315]. In early years of cancer study, it had been believed that cancer cells were anaerobic tissues. But, it is now believed by the above reports that nutrition and oxygen supply is essential for the growth of a tumor.

German research scientists reported in 1993 that they separated a chemical compound inhibiting angiogenesis from a bean [T. Fotsis, et al., *Proc. Natl. Acad. Sci. USA,* 1993, 90: 2690]. The compound was named 'genistein', which has been expected to suppress the growth of a small malignant tumor. The number of prostatic cancer patients among Japanese taking beans a lot is less than that of Westerners. But, the number of prostatic cancer patients among Japanese immigrants in western countries increased fast since they no more took beans frequently [F. M. Uckun, et al., *Science,* 1995, 267: 886]. Another study group lead by Dr. Fatih M. Uckun at University of Minnesota reported in 1995 that they prepared a medicine by combining a monoclonal antibody with genistein and administered the medicine to a mouse transplanted with human BCP leukemia cells, resulting in 99.999% destruction of human BCP leukemia cells [F. M. Uckun, et al., *Science,* 1995, 267: 886].

Thus, an angiogenesis inhibitor is not only a relevant factor to explain the mechanism of cancer cell growth but also used effectively for the prevention and the treatment of cancers and further for the treatment of angiogenesis related diseases such as diabetic retinopathy, rheumatoid arthritis, chronic inflammation, hemangioma, etc. For that reason, an angiogenesis inhibitor has been a major target of study in the field of biological science as well as in the field of industry.

SUMMARY OF THE INVENTION

It is an object of the present invention to provide a novel compound and methods for suppressing metastasis and angiogenesis.

DETAILED DESCRIPTION OF PREFERRED EMBODIMENTS

In order to achieve the above object, the present invention provides a cancer cell migration inhibitor containing diaryl-isoxazole derivatives as an effective ingredient.

The present invention also provides an angiogenesis inhibitor containing diaryl-isoxazole derivatives as an effective ingredient.

The invention provides a pharmaceutical composition comprising a diaryl-isoxazole derivative and a pharmaceutically acceptable carrier. The composition is suitable for a variety of uses including, but not limited to, inhibition of cancer cell migration, inhibition of angiogenesis, and inhibition of related diseases. Such methods comprise contacting cells to be treated with an effective amount of a diaryl-isoxazole derivative of the invention. The pharmaceutical composition of the invention can be used in prophylactic and therapeutic treatment of such diseases.

Hereinafter, the present invention is described in detail.

The present invention provides a cancer cell migration inhibitor containing a compound represented by the following <Formula 1> as an effective ingredient.

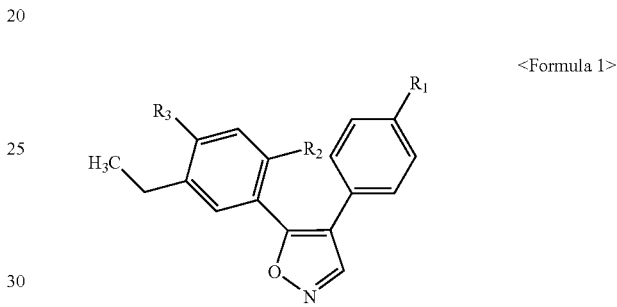

<Formula 1>

(Wherein, $R_1$ and $R_2$ are each independently, hydroxy, $C_1$~$C_{10}$ alkyl, $C_1$~$C_{10}$ alkoxy, $C_1$~$C_5$ alkyl substituted by phenyl having 1~3 substituents, $C_1$~$C_5$ alkoxy substituted by phenyl having 1~3 substituents, or halogen atom, $R_3$ is hydroxy, $C_1$~$C_{10}$ alkyl, $C_1$~$C_{10}$ alkoxy, $C_1$~$C_5$ alkyl substituted by phenyl having 1~3 substituents, or $C_1$~$C_5$ alkoxy substituted by phenyl having 1~3 substituents.)

Preferably, the compounds of the <Formula 1> comprise:

(1) 5-(5-ethyl-2-hydroxy-4-methoxyphenyl)-4-(4-methoxyphenyl)isoxazole, (2) 5-(2,4-dimethoxy-5-ethylphenyl)-4-(4-bromophenyl)isoxazole, (3) 5-(2,4-dimethoxy-5-ethylphenyl)-4-(4-methoxyphenyl)isoxazole, (4) 5-(2-benzyloxy-5-ethyl-4-methoxyphenyl)-4-(4-methoxyphenyl)isoxazole, (5) 5-(5-ethyl-2-hydroxy-4-methoxyphenyl)-4-(4-hydroxyphenyl)isoxazole, or (6) 5-(2,4-dihydroxy-5-ethylphenyl)-4-(4-hydroxyphenyl)isoxazole.

The compound of <Formula 1> of the present invention has an activity of suppressing cancer cells. As shown in FIG. 1, one of the compounds of the present invention, 5-(5-ethyl-2-hydroxy-4-methoxyphenyl)-4-(4-methoxyphenyl)isoxazole(1), inhibited migration of breast cancer cells (MDA-MB-231) up to 50% with the concentration of 50 nM, suggesting that the compound has excellent activity of inhibiting cancer cell migration. Owing to such excellent activity of suppressing cancer cells, the compound of the present invention can be used as an anticancer agent inhibiting cancer cell migration.

The present invention also provides an angiogenesis inhibitor containing the compound of <Formula 1> as an effective ingredient.

As explained above, the compound of the present invention has an activity of suppressing both cancer cell migration and angiogenesis at the same time. As shown in FIG. 2 and FIG. 3, the compound of the present invention inhibited tube formation in HUVECs at the concentration of 100 nM. As shown in FIG. 4, 5-(5-ethyl-2-hydroxy-4-methoxyphenyl)-4-(4-methoxyphenyl)isoxazole(1) inhibited angiogenesis in zebrafish up to 50% at the concentration of 500 nM. Those results indicate that the compound of the present invention can be used as an angiogenesis inhibitor, and in particular, the compound can be effectively used for the prevention and for the treatment of angiogenesis related diseases such as cancer, rheumatoid arthritis, psoriasis or angiogenesis diseases caused in eyeball, etc.

The compound of the <Formula 1> of the present invention can be administered orally or parenterally and be used in general form of pharmaceutical formulation. The compound of the present invention can be prepared for oral or parenteral administration by mixing with generally used fillers, extenders, binders, wetting agents, disintegrating agents, diluents such as surfactant, or excipients. Solid formulations for oral administration are tablets, pill, dusting powders, capsules and troches. These solid formulations are prepared by mixing one or more suitable excipients such as starch, calcium carbonate, sucrose, lactose, or gelatin, etc. Except for the simple excipients, lubricants, for example magnesium stearate, talc, etc, can be used. Liquid formulations for oral administrations are suspensions, solutions, emulsions and syrups, and the above mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, freeze drying agents and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, xvitepsol, macrogol, tveen 61, cacao butter, laurin butter, glycerol, gelatin, etc.

The effective dosage of the compound represented by <Formula 1> might be determined by a practitioner in consideration of age, weight, gender and body condition of a patient, administration method and severity of a disease. For example, the effective dosage of the compound for an adult with 70 kg is 100-1000 mg/day in general, but the dosage of 100-500 mg/day is more preferred. Administration times can be either once a day or several times a day according to a doctor's or a pharmacist's consideration.

BRIEF DESCRIPTION OF THE DRAWINGS

The application of the preferred embodiments of the present invention is best understood with reference to the accompanying drawings, wherein:

FIG. 1 is a graph showing the inhibition of breast cancer cell migration by the compound of Example 1 of the present invention, FIG. 2 is a set of photographs showing the inhibition of tube formation in HUVEC by the compound of Example 1 of the present invention, FIG. 3 is a set of photographs showing the inhibition of angiogenesis in HUVEC by the compounds of Example 1~Example 6 of the present invention, FIG. 4 is a set of photographs showing the inhibition of angiogenesis in zebrafish by the compound of Example 1 of the present invention.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of 5-(5-ethyl-2-hydroxy-4-methoxyphenyl)-4-(4-methoxyphenyl)isoxazole The compound of the invention was prepared by the reaction procedure described in the below scheme 1.

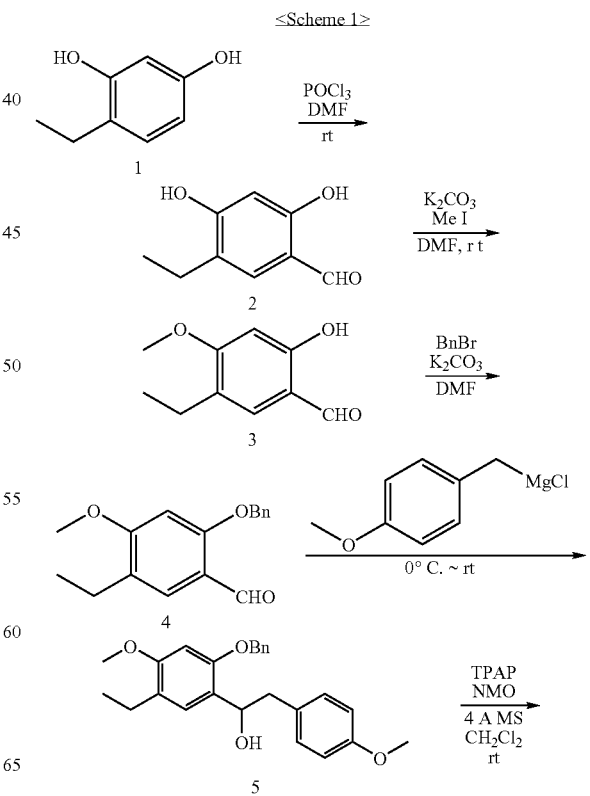

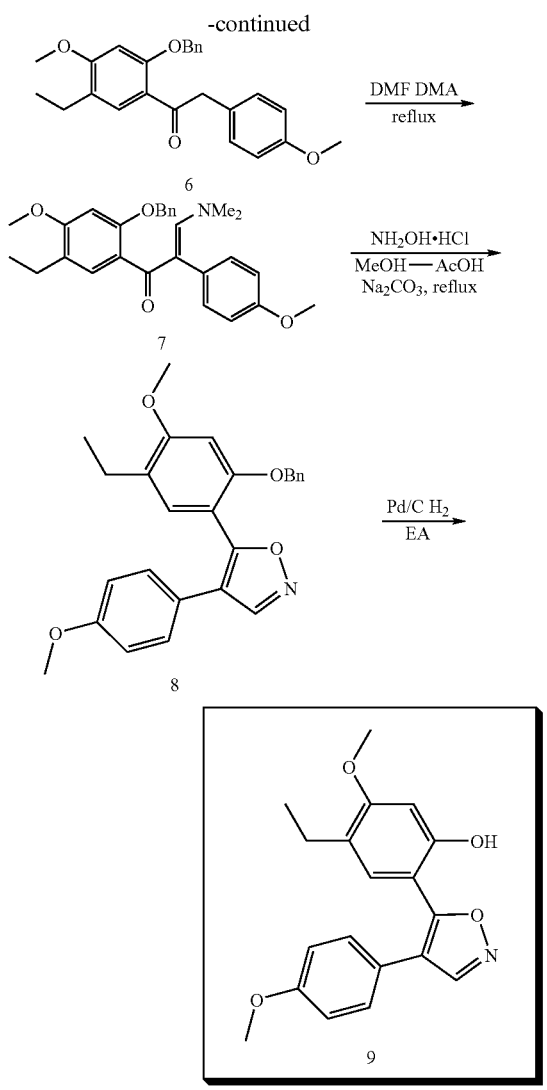

Particularly, 14.5 ml (0.18 mol) of dried dimethylformaldehyde was put in a 10° C. water bath and 4.43 ml (0.078 mol) of POCl₃ was slowly added therein, followed by stirring for 30 minutes. 3.0 g (0.022 mol) of 4-ethylresorcinol was slowly added in 14.5 ml (0.18 mol) of dimethylformaldehyde, and the mixture was stirred at room temperature for 1 hour outside the water bath. The solution was put in a 0° C. water bath again and 2 M NaOH aqueous solution was added to quench the reaction. The reaction solution was diluted with ethyl acetate, followed by two times extraction with 2 M NaOH aqueous solution. The aqueous solution was neutralized by 3 N HCl, which was extracted four times by ethyl acetate and washed with brine. Combined organic layer was dried over anhydrous magnesium sulfate, filtered, and concentrated under reduced pressure. The concentrated solution was purified by silica-gel column chromatography (hexane:ethyl acetate=7:1), to give 2.5 g of compound 2 (yield: 62%).

2.55 g (0.015 mol) of the compound 2 and 4.24 g (0.03 mol) of potassium carbonate were dissolved in dimethylformaldehyde (25 ml). 2.28 g (0.016 mol) of methyl iodide was added therein, and the reaction mixture was stirred at room temperature for 5 hours. The reaction solution was filtered to remove inorganic salts, and 200 ml of water was added. Extraction was performed three times with ethyl acetate and then washed with brine. Combined organic layer was dried over anhydrous magnesium sulfate, filtered, and concentrated under reduced pressure. The concentrated solution was purified by silica-gel column chromatography (hexane:ethyl acetate=20:1), to give 1.6 g of compound 3 (yield: 54%).

2.1 g (0.012 mol) of the compound 3 and 4.8 g (0.035 mol) of potassium carbonate were dissolved in dimethylformaldehyde (20 ml). 2.28 g (0.016 mol) of benzylbromide was added therein, and the reaction mixture was stirred at room temperature for 1 hour. The reaction solution was filtered to remove inorganic salts, and 200 ml of water was added. Extraction was performed three times with ethyl acetate and then washed with brine. Combined organic layer was dried over anhydrous magnesium sulfate, filtered, and concentrated under reduced pressure. The concentrated solution was purified by silica-gel column chromatography (hexane:ethyl acetate=5:1), to give 3.0 g of compound 4 (yield: 94%).

5 ml of tetrahydrofuran was added to 0.75 g (0.031 mol) of magnesium, to which 0.6 g (3.8 mmol) of 4-methoxybenzylchloride was slowly added. 1.0 g (6.4 mmol) of 4-methoxybenzylchloride was diluted with 10 ml of tetrahydrofuran, then, added to the above mixture. The reaction solution was refluxed with heating for one hour and then cooled down in a 0° C. water bath. The ashy solution was extracted by using a syringe, which was used as a grignard reagent. 0.92 g (3.4 mmol) of the compound 4 was dissolved in 15 ml of tetrahydrofuran, which was stored in a 0° C. water bath. After adding the grignard reagent slowly, the solution was taken out of the water bath, followed by stirring at room temperature for 1 hour. Saturated ammonium chloride solution was added to the reaction solution. Extraction with ethyl acetate was performed three times and washed with brine. Combined organic layer was dried over anhydrous magnesium sulfate, filtered, and concentrated under reduced pressure. The concentrated solution was purified by silica-gel column chromatography (hexane:ethyl acetate=7:1), to give 1.3 g of compound 5 (yield:97.4%).

1.3 g (3.3 mmol) of compound 5, 0.57 g (4.9 mmol) of 4-methylmorpholine N-oxide and 1.64 g of 4 Å molecular sieves in the form of anhydrous powder were all dissolved in 6.54 ml of dichloromethane ($CH_2Cl_2$). After adding 57 mg of tetrapropylammonium perruthenate thereto, the mixture was stirred for 30 minutes. The reaction solution was washed with ethyl acetate using a short silica-gel pad, filtered and concentrated, to give 1.2 g of compound 6 (yield: 93.1%).

1.2 g (3.0 mmol) of compound 6 was dissolved in toluene, to which 5.3 ml (40 mmol) of dimethylformaldehyde dimethylacetal was added slowly. The reaction mixture was refluxed with heating for 16 hours at 135° C. The reaction solution was cooled down, concentrated and purified by silica-gel column chromatography, to give 0.94 g of compound 7 (yield: 70%).

0.94 g (2.1 mmol) of compound 7 was dissolved in methanol (35 ml) and water (11 ml), and then 70.5 mg (1.2 mmol) of sodium carbonate and 1.6 g (2.3 mmol) of NH$_2$OH.HCl were added, followed by stirring. pH of the solution was adjusted to 4-5 using acetic acid, and the mixture was refluxed with heating for 2 hours. The reaction solution was cooled down and pH was adjusted once again to 8 using saturated ammonium hydroxide aqueous solution. Extraction with dichloromethane was performed four times. The extract was dried over anhydrous sodium sulfate, filtered and concentrated. The concentrated solution was purified by silica-gel column chromatography, to give 0.8 g of compound 8 (yield: 90.50/%).

0.8 g (1.9 mmol) of compound 8 was dissolved in ethyl acetate (10 ml) and then 40 mg of 10% Palladium/c was added thereto. The reaction was performed under 50 psi of hydrogen atmosphere for 14 hours. The reaction solution was washed with ethyl acetate using a short silica-gel pad, filtered and concentrated, to give 0.57 g of the final compound 9 (yield 92%).

m.p.: 149-150° C.

$^1$H NMR (CDCl$_3$) δ8.35 (s, 1H), 7.28 (dd, J=6.9, 2.4 Hz, 2H), 7.06 (s, 1H), 6.88 (dd, J=6.9, 2.4 Hz, 2H), 6.48 (s, 1H), 3.80 (s, 6H), 2.42 (q, J=7.2 Hz, 2H), 0.98 (t, J=7.2 Hz, 3H) ppm.

$^{13}$C NMR (CDCl$_3$) δ162.3, 160.3, 159.4, 153.6, 151.5, 129.3, 128.5, 125.2, 121.6, 115.2, 114.4, 105.3, 99.6, 55.3, 55.2, 22.0, 13.7 ppm.

Example 2

Preparation of 5-(2,4-dimethoxy-5-ethylphenylo-4-(4-Bromophenyl)isoxazole

A target compound was prepared by the same method as described in the above Example 1 except that 4-methoxybenzylchloride used in Example 1 was substituted with 4-bromobenzylchloride.

m.p.: 102-103° C.,

The compound was confirmed by mass analysis to have molecular weight of 373 and M+2 of the compound was 375.

Example 3

Preparation of 5-(2,4-dimethoxy-5-ethylphenylb-4-(4-methoxyphenyl)isoxazole

A target compound was prepared by the same method as described in the above Example 1 except that 4-ethylresocinol used in Example 1 was substituted with 3,4-dimethoxyethylbenzene.

m.p.: 72-73° C.

$^1$H NMR (CDCl$_3$) δ8.42 (s, 1H), 7.25 (s, 1H), 7.20 (d, J=8.1 Hz, 2H), 6.84 (d, J=8.1 Hz, 2H), 6.43 (s, 1H), 3.87 (s, 3H), 3.79 (s, 3H), 3.51 (s, 3H), 2.56 (q, J=7.2 Hz, 2H), 1.15 (t, J=7.2 Hz, 3H) ppm.

$^{13}$C NMR (CDCl$_3$) δ162.3, 159.9, 158.6, 156.3, 150.5, 130.6, 128.2, 124.9, 123.4, 116.3, 113.7, 109.6, 95.2, 55.4, 55.3, 55.1, 22.2,14.0 ppm.

Example 4

Preparation of 5-(2-benzyloxy-5-ethyl-4-methoxyphenyl)-4-(4-methoxyphenyld)isoxazole A target compound was prepared by the same method as described in the above Example 1 except that 4-ethylresocinol used in Example 1 was substituted with 3-methoxy-4-benzyloxyethylbenzene.

m.p.: 99-100° C.

$^1$H NMR (CDCl$_3$) δ8.42 (s, 1H), 7.25-7.00 (m, 8H), 6.78 (dd, J=6.9, 2.4 Hz, 2H), 6.48 (s, 1H), 4.84 (s, 2H), 3.80 (s, 3H), 3.78 (s, 3H), 2.56 (q, J=7.2 Hz, 2H), 1.14 (t, J=7.2 Hz, 3H) ppm.

$^{13}$C NMR (CDCl$_3$) δ162.3, 159.7, 158.7, 155.5, 150.5, 136.5, 130.8, 128.2, 127.6, 127.0, 125.3, 123.3, 116.6, 113.8, 109.3, 97.0, 70.7, 55.3, 55.2, 22.3, 14.0 ppm.

Example 5

Preparation of 5-(5-ethyl-2-hydroxy-4-methoxyphenyl)-4-(4-hydroxyphenyld)isoxazole A target compound was prepared by the same method as described in the above Example 1 except that 4-methoxybenzylchloride used in Example 1 was substituted with 4-benzyloxybenzylchloride.

m.p.: 146-147° C.

$^1$H NMR (CD$_3$OD) δ8.57 (s, 1H), 7.17 (dd, J=6.6, 2.4 Hz, 2H), 6.97 (s, 1H), 6.70 (dd, J=6.6, 2.4 Hz, 2H), 6.48 (s, 1H), 4.86 (brs, 2H), 3.81 (s, 3H), 2.48 (q, J=7.2 Hz, 2H), 1.06 (t, J=7.2 Hz, 3H) ppm.

$^{13}$C NMR (CD$_3$OD) δ161.3, 157.9, 156.2, 151.5, 131.3, 129.5, 125.2, 122.8, 118.1, 116.3, 108.0, 100.0, 55.7, 23.3, 14.7 ppm.

Example 6

Preparation of 5-(2,4-dihydroxy-5-ethylphenyl)-4-(4-hydroxyphenyld)isoxazole

A target compound was prepared by the same method as described in the above Example 1 except that 4-ethyltesocinol used in Example 1 was substituted with 3,4-dibenzyloxybenzylchloride, and 4-methoxybenzylchloride used in Example 1 was substituted with 4-benzyloxybenzylchloride.

m.p.: 85-86° C.

$^1$H NMR (CD$_3$OD) δ8.56 (s, 1H), 7.18 (dd, J=8.4 Hz, 2H), 6.92 (s, 1H), 6.71 (dd, J=8.4 Hz, 2H), 6.39 (s, 1H), 2.48 (q, J=7.2 Hz, 2H), 1.08 (t, J=7.2 Hz, 3H) ppm.

$^{13}$C NMR (CD$_3$OD) δ164.4, 159.2, 157.8, 155.8, 151.4, 131.7, 129.5, 123.9, 122.9, 117.8, 116.3, 107.6, 103.8, 23.3, 14.7 ppm.

Manufacturing Example 1

Preparation of Capsules 5 mg of the compound prepared in Example 1 was mixed with 14.8 mg of lactose, 10.0 mg of polyvinyl pyrrolidone and 0.2 mg of magnesium stearate. The mixture was put tightly in a solid No. 5 gelatin capsule.

The constituents of the powders and capsules are as follows.

| | |
|---|---|
| Compound of Example 1 | 5.0 mg |
| Lactose | 14.8 mg |
| Polyvinyl pyrrolidone | 10.0 mg |
| Magnesium stearate | 0.2 mg |

Manufacturing Example 2

Preparation of Injectable Solutions 10 mg of the compound of Example 1 was mixed with 180 mg of mannitol, 26 mg of $Na_2HPO_4.12H_2O$ and 2974 mg of distilled water, resulting in an injectable solution. The solution was put in a bottle and sterilized by heating at 20° C. for 30 minutes.

The constituents of the injectable solutions are as follows.

| | |
|---|---|
| Compound of Example 1 | 100 mg |
| Mannitol | 180 mg |
| $Na_2HPO_4.12H_2O$ | 26 mg |
| Distilled water | 0.2 mg |

Experimental Example 1

Analysis of Cell Migration

In order to investigate cell migration, modified Boyden chamber and 8 μm pore membrane were purchased from Neuro probe Co. and staining solution for cell staining, Giemsa solution, was purchased from Sigma Co. Other instruments used were $CO_2$ incubator for cell culture, centrifuge for cell washing and inverted microscope (TE 300, Nikon, Japan) for observation.

Particularly, 90% grown up cells on a culture plate were isolated using trypsin/EDTA. The cells were treated with soybean trypsin inhibitor, and washed with serum free medium three times. Then, cell density was adjusted to $4 \times 10^5$ cells/ml. The compounds of Example 1-6 and a medium supplemented with 10% FBS were put by 30 μl each in a chamber well of the bottom of modified Boyden chamber, on which 8 μm pore membrane was put. Silicon gasket was placed over and finally a top plate was put on the gasket and fastened with a nut. The cultured cells were put in a well of top plate by 50 μl. The chamber was rapped and further cultured in a 37° C. 5% $CO_2$ incubator for 18 hours.

18 hours later, the nut was taken out. Membrane was separated and fixed in methanol for 10 minutes, followed by drying in the air. After membrane was completely dried, it was stained in Giemsa solution for 90 minutes. At that time, the staining solution was diluted with distilled water at the ratio of 1:10 before use. Upon competing staining, the membrane was dipped in distilled water for about 10 seconds for washing. The membrane was put on a cover slip with a part having cells not shifted heading up and scrubbed with a cotton swab carefully. Manicure was put on the edge of the cover slip, which was then fixed well on a slide glass.

The number of migrated cells on the sample prepared above was investigated under inverted microscope.

Inhibition of migration of cancer cells and smooth muscle cells by the compounds of Example 1-6 was investigated by the method described above and cell migration inhibition rate was calculated by the below <Mathematical Formula 1>.

<Mathematical Formula 1>

Cell migration inhibition rate (%)=100−[Number of migrated cells treated with test samples/Number of migrated cells of control]×100

For a control group, only 1% dimethyl sulfoxide PMSO) was added instead of a compound of the present invention.

The results were represented in FIG. 1 and Table 1.

TABLE 1

| Compound | 1 uM | 10 uM |
|---|---|---|
| Example 1 | 92.30% | 94.50% |
| Example 2 | 90.80% | 94.80% |
| Example 3 | 68.40% | 82.50% |
| Example 4 | 54.60% | 70.10% |
| Example 5 | 43.50% | 43.30% |
| Example 6 | 79.50% | 79.40% |

FIG. 1 is a graph showing inhibition of migration of breast cancer cell line (MDA-MB-231) according to the different concentrations of the compound of Example 1. As shown in FIG. 1, inhibition of breast cancer cells increases with the increase of the concentration of the compound of Example 1. In particular, the compound inhibited breast cancer cell migration up to 50% at the concentration of 50 nM, indicating that the compound has excellent inhibition effect on cell migration.

Table 1 also shows inhibition of migration of breast cancer cells by 1 μM and 10 μM each of the compounds of Example 1-6. As shown in Table 1, not only the compound of Example 1 but also other compounds of Example 2-6 have excellent inhibition effect on breast cancer cell migration.

Experimental Example 2

Investigation of Angiogenesis Inhibition Activity of the Compound of the Present Invention by in vitro Endothelial Morphogenesis Assay Angiogenesis inhibition activity of the compound of the present invention was investigated by in vitro endothelial morphogenesis assay using human originated cell line HUVEC.

24-well cell culture plate and matrigel matrix were purchased from BD biosciences Co. Other instruments used for the experiments were $CO_2$ incubator for cell culture and inverted microscope (TE 300, Nikon, Japan) equipped with a digital camera for observation and confirmation of the result.

Particularly, starvation of HUVECs on a serum free medium was performed for overnight. Each well of 24-well cell culture plate was coated with 0.2 Ml of matrigel matrix, which was cultured in a 37° C. incubator for 1 hour. 0.2 Ml of cell culture solution with the cell density of 20000 was put in each well, which was further cultured in a $CO_2$ incubator for 30 minutes. Then, a fresh medium, which was diluted with different concentrations of the compounds of Example 1-6, was given to each well. 1% serum was added to the wells, followed by further culture for 24 hours. Tube formation by HUVECs is observed. In this invention, inhibition of tube formation by the compound of the present invention was observed under inverted microscope, and the results were shown in FIG. 2 and FIG. 3. FIG. 2 is a photograph showing inhibition of angiogenesis in vascular endothelial cells according to the concentration the compound of Example 1, and FIG. 3 is a photograph showing inhibition of angiogenesis in vascular endothelial cells by 1 μM of the compounds of Example 1-6.

As shown in FIG. 2, tube formation in vascular endothelial cells was inhibited by the compound of Example 1. Particularly, inhibition of tube formation in vascular endothelial cells was already detected at the concentration of 0.01 μM, and tube began to break to be like a water drop with the increase of the concentration.

As shown in FIG. 3, not only the compound of Example 1 but also other compounds of Example 2-6 inhibited tube formation in vascular endothelial cells.

Experimental Example 3

Investigation of Angiogenesis Inhibition Activity of the Compound of the Present Invention by using Zebrafish The angiogenesis inhibition activity of the compound of Example 1 was observed in zebrafish.

Experimental instruments used for the invention were temperature-controlled incubator for the incubation of embryo and inverted microscope (TE 300, Nikon, Japan) equipped with a digital camera for observation and confirmation for the results.

Embryos of zebrafish were loaded on a 96-well plate by three embryos per well. The embryos were confirmed to be synchronized embryos which means one day has passed after development. The compounds of the present invention were dissolved in 0.1% DMSO to prepare different concentrations for each compound. Each compound was treated to 4 wells and inhibition of subintestinal vessels (SIVs) in 12 embryos was investigated. To prepare a control, 8 wells were treated with 0.1% DMSO (in embryo water: 0.2 g/l instant ocean salt) (Randall T. Peterson, et al, *Proc. Natl. Aced. Sci. USA*, 2000, 97: 12965).

For the observation of angiogenic vessels (SIVs), an rmmunological approach of Catherine E. Willet, et al. (Catherine E. Willet, et al., *Angiogenesis*, 1999, 3: 353), was used in the present invention. Particularly, three days after development, an embryo was fixed in 4% paraformaldehyde at room temperature for 2 hours. The embryo was washed twice with PBS, and dehydrated step by step with PBS, 25%, 50%, 75% and 100% methanol. Then, the embryo was rehydrated step by step with 100%, 75%, 50% and 25% methanol and PBS. The embryo was stabilized, for staining, in NTMT buffer solution (0.1 M Tris-HCl pH 9.5; 50 mM MgCl; 0.1 M NaCl; 0.1% Tween 20) at room temperature for 45 minutes. 4.5 μl of 75 mg/Ml NBT and 3.5 μl of 50 mg/Ml X-phosphate were added to the stabilized embryo. After staining the embryo for 10-20 minutes, PBST (PBS; 0.5% Tween 20) was added to quench the reaction. Melanin was removed and the embryo was treated with a mixed solution (PBS supplemented with 5% formamide and 10% $H_2O_2$) for better observation of blood vessels. SIVs of the embryo were observed under inverted microscope. And the results were shown in FIG. 4.

After comparing the arrow-marked part in FIG. 4 with a control, the compound of Example 1 of the present invention was proved to have excellent angiogenesis inhibition activity. In fact, the compound inhibited angiogenesis in zebrafish at the concentration of 0.5 μM.

Experimental Example 4

Acute Oral Toxicity Test in Rats 6-week old SPF (specific pathogen-free) SD line rats were used in the acute toxicity test. Compound 1 of the present invention was suspended in 0.5% methylcellulose solution and orally administered once to 2 rats per group. Death, clinical symptoms, and weight change in rats were observed, hematological tests and biochemical tests of blood were performed, and any abnormal signs in the gastrointestinal organs of chest and abdomen were checked with eyes during autopsy.

The results showed that the test compound did not cause any specific clinical symptoms, weight change, or death in rats. No change was observed in hematological tests, biochemical tests of blood, and autopsy. The compound used in this experiment was evaluated to be safe substance since it did not cause any toxic change in rats up to the level of 1000 mg/kg and its estimated $LD_{50}$ value was much greater than 1500 mg/kg in rats.

INDUSTRIAL APPLICABILITY

As explained hereinbefore, diaryl-isoxazole derivatives of the present invention inhibit migration of breast cancer cell lines and angiogenesis as well, so that they can be effectively used as a metastasis inhibitor and further for the prevention and the treatment of angiogenesis related diseases including cancers, rheumatoid arthritis, psoriasis or angiogenesis diseases caused on eyeball.

What is claimed is:

1. A pharmaceutical composition for inhibiting breast cancer cell migration which is selected from the group consisting of 1) 5-(5-ethyl-2-hydroxy-4-methoxyphenyl)-4-(4-methoxyphenyl)isoxazole; 2) 5-(2,4-dimethoxy-5-ethylphenyl)-4-(4-bromophenyl)isoxazole; 3) 5(2,4-dimethoxy-5-ethylphenyl)-4-(4-methoxyphenyl)isoxazole; 4) 5-(2-benzyloxy-5-ethyl-4-methoxyphenyl)-4-(4-methoxyphenyl)isoxazole; 5) 5-(5-ethyl-2-hydroxy-4-methoxyphenyl)-4-(4-hydrophenyl)isoxazole; and 6) 5-(2,4-dihydroxy-5-etylphenyl)-4-(4-hydroxyphenyl)isoxazole as an effective ingredient.

2. The pharmaceutical composition as set forth in claim 1, wherein the pharmaceutical composition is used as a breast cancer migration inhibition agent.

3. The pharmaceutical composition of claim 1, wherein the compound is 5-(5-ethyl-2-hydroxy-4-methoxyphenyl)-4-(4methosyphenyl)isoxazole.

* * * * *